United States Patent
Yu et al.

(10) Patent No.: US 11,373,367 B2
(45) Date of Patent: Jun. 28, 2022

(54) METHOD FOR CHARACTERIZATION OF RESPIRATORY CHARACTERISTICS BASED ON VOXEL MODEL

(71) Applicant: SOOCHOW UNIVERSITY, Suzhou (CN)

(72) Inventors: Shumei Yu, Suzhou (CN); Pengcheng Hou, Suzhou (CN); Rongchuan Sun, Suzhou (CN); Shaolong Kuang, Suzhou (CN); Lining Sun, Suzhou (CN)

(73) Assignee: SOOCHOW UNIVERSITY, Suzhou (CN)

(*) Notice: Subject to any disclaimer, the term of this patent is extended or adjusted under 35 U.S.C. 154(b) by 0 days.

(21) Appl. No.: 17/056,758

(22) PCT Filed: Nov. 20, 2019

(86) PCT No.: PCT/CN2019/119693
§ 371 (c)(1),
(2) Date: Nov. 18, 2020

(87) PCT Pub. No.: WO2021/077515
PCT Pub. Date: Apr. 29, 2021

(65) Prior Publication Data
US 2021/0375037 A1    Dec. 2, 2021

(30) Foreign Application Priority Data
Oct. 25, 2019    (CN) .......................... 201911023806.1

(51) Int. Cl.
*G06T 17/10*    (2006.01)
*G06T 7/55*    (2017.01)
(Continued)

(52) U.S. Cl.
CPC .............. *G06T 17/10* (2013.01); *G06T 5/002* (2013.01); *G06T 5/20* (2013.01); *G06T 7/0012* (2013.01);
(Continued)

(58) Field of Classification Search
CPC ..................................................... G06T 17/10
See application file for complete search history.

(56) References Cited

U.S. PATENT DOCUMENTS

| | | | |
|---|---|---|---|
| 2015/0139503 A1* | 5/2015 | Kabus | G06T 7/30 382/107 |
| 2018/0315188 A1* | 11/2018 | Tegzes | G06K 9/2054 |

FOREIGN PATENT DOCUMENTS

| | | |
|---|---|---|
| CN | 103761745 A | 4/2014 |
| CN | 104395933 A | 3/2015 |

(Continued)

*Primary Examiner* — Shivang I Patel
(74) *Attorney, Agent, or Firm* — SZDC Law PC (57) ABSTRACT

A method for characterization of respiratory characteristics based on a voxel model includes: successively capturing multiple frames of depth image of a thoracoabdominal surface of human body and modelling the multiple frames of depth image in 3D to obtain multiple frames of voxel model in time series; traversing voxel units of the multiple frames of voxel model and extracting a volumetric characteristic and areal characteristic of the multiple frames of voxel model; acquiring a minimum common voxel bounding box of the multiple frames of voxel model; describing spatial distribution of the multiple frames of voxel model in the form of probability and arranging the probabilities of the minimum voxel bounding boxes of individual frames of voxel model to construct a sample space of super-high dimensional vectors; reducing the dimensions of the sample space to obtain intrinsic parameters; obtaining a characteristic variable capable of characterizing the voxel model.

7 Claims, 5 Drawing Sheets

(51) Int. Cl.
*G06T 5/00* (2006.01)
*G06T 5/20* (2006.01)
*G06T 7/00* (2017.01)

(52) U.S. Cl.
CPC ...... *G06T 7/55* (2017.01); *G06T 2207/10024* (2013.01); *G06T 2207/10028* (2013.01)

(56) References Cited

FOREIGN PATENT DOCUMENTS

| | | | |
|---|---|---|---|
| CN | 107403407 | A | 11/2017 |
| CN | 109069858 | A | 12/2018 |
| WO | 2018172229 | A1 | 9/2018 |

* cited by examiner

METHOD FOR CHARACTERIZATION OF RESPIRATORY CHARACTERISTICS BASED ON VOXEL MODEL

This application is the National Stage Application of PCT/CN2019/119693, filed on Nov. 20, 2019, which claims priority to Chinese Patent Application No. 201911023806.1, filed on Oct. 25, 2019, which is incorporated by reference for all purposes as if fully set forth herein.

FIELD OF THE INVENTION

The present invention relates to the field of respiration tracking of radiotherapy robots, and more particularly to a method for characterization of respiratory characteristics based on a voxel model.

DESCRIPTION OF THE RELATED ART

Respiration tracking for tumor motion is one of the critical techniques for fulfilling precision radiotherapy by radiotherapy robots. In a currently most mainstream approach, a model of association body-surface marking points with internal tumors is utilized to predict in advance the position where the tumor has arrived and plan movement of the robotic arm, so that the beam from a linear accelerator can track the tumor motion in real time, thereby accomplishing precision radiotherapy. However, tumor respiratory motion modelling is rather complicated and presents individual differences, and the method for characterization of respiratory characteristics by use of limited body-surface marking points cannot provide comprehensive characterization of non-plane motion information, causing poor accuracy and robustness of clinical data.

A method for characterization that can reflect more comprehensive body-surface motion information has to be continuously explored in order to achieve better accuracy and robustness. The research on a method for characterization of comprehensive body-surface motion information is orientated mainly in two directions. One is focused on the number of the limited body-surface marking points. For example, 3, 6, 19 etc. body-surface marking points are utilized to characterize body-surface motion information. The other is focused on the method for characterization of body-surface motion information based on a multimodal sensor. Multiple types of sensors, including a tension band secured to the thoracoabdominal surface, an optical marking point, an acceleration sensor, an airflow acceleration and temperature sensor secured around the nostrils, or the like, are utilized and information from these sensors are merged to characterize the body-surface motion. Research on the method for characterization of multimodal information suggests that body-surface marking point motion information has better association with the tumor location; and research on the method for characterization of body-surface marking points suggests that the greater the number of the marking points, the more comprehensive the representation of respiratory motion characteristics, but limited body-surface marking point information still fails to reflect accurately the pattern of variation in body-surface respiratory motion.

Therefore, the research on the method for characterization of body-surface respiratory characteristics is important for improving accuracy and robustness of tumor motion respiration tracking in radiotherapy robots.

SUMMARY OF THE INVENTION

A problem to be solved by the present invention is to provide a method for characterization of respiratory characteristics based on a voxel model, and this method can comprehensively characterize body-surface respiratory motion information and thus has wide application.

To address the technical problem mentioned above, the present invention provides a method for characterization of respiratory characteristics based on a voxel model, including the steps of:

successively capturing, by a camera, multiple frames of depth image of a thoracoabdominal surface of human body and modelling the multiple frames of depth image in 3-Dimensions (3D) to obtain multiple frames of voxel model in time series;

traversing a voxel unit of the multiple frames of voxel model and extracting a volumetric characteristic and areal characteristic of the multiple frames of voxel model;

acquiring a minimum common voxel bounding box of the multiple frames of voxel model;

describing spatial distribution of the multiple frames of voxel model in the form of probability and arranging the probabilities of the minimum voxel bounding box of each frame of voxel model to construct a sample space of superhigh-dimensional vectors;

reducing the dimensions of the sample space to obtain intrinsic parameters after dimensionality reduction; and obtaining a characteristic variable capable of characterizing the voxel model according to the intrinsic parameters, the volumetric characteristic, and the areal characteristic.

Preferably, the "volumetric characteristic" is the overall volumetric variation state characteristic of the multiple frames of voxel model.

Preferably, the "areal characteristic" is the overall outer-layer surface area variation state characteristic of the multiple frames of the voxel model.

Preferably, the "successively capturing, by a camera, multiple frames of depth image of a thoracoabdominal surface of a human body and modelling the multiple frames of depth image in 3D to obtain multiple frames of voxel model in time series" specifically includes the following steps:

S11 successively capturing, by two stationary RGB-D cameras, multiple frames of depth image of thoracoabdominal surface of human body in motion;

S12 denoising point cloud data in the depth image through a filter algorithm, smoothening the point cloud through a moving least square method, and merging the point cloud data through an ICP algorithm;

S13 splitting human body data from medical platform background data in the depth image through threshold filtering;

S14 constructing a surface model into a closed model through border interpolation;

S15 quick fitting the three-dimensional curved surface of the human body surface through Poisson's reconstruction; and S16 building a three-dimensional voxel model of thoracoabdominal part of human body through an Octomap to obtain multiple frames of voxel model in time series.

Preferably, the "acquiring a minimum common voxel bounding box of the multiple frames of voxel model" specifically includes:

representing each frame of voxel model by $M_i$ and letting $M_i \in M$, M being the voxel model of all the frames;

traversing M, calculating the minimum bounding box of $M_i$, recording the length $L_{M_i}$, width $W_{M_i}$, and height $H_{M_i}$ of the minimum bounding box, letting $L_{M_i} \in L$, $W_{M_i} \in W$, $H_{M_i} \in H$, where L is the set of the lengths of the minimum bounding boxes of all the frames of voxel model, W is the set of the widths of the minimum bounding boxes of all the frames of voxel model, and H is the set of the heights of the minimum bounding boxes of all the frames of voxel model; and finding $L_{max}$, $L_{min}$, $W_{max}$, $W_{min}$, $H_{max}$, $H_{min}$ in L, Q, H to construct a minimum common voxel bounding box B that partitions the space according to the voxel resolution of M.

Preferably, the "describing spatial distribution of the multiple frames of voxel model in the form of probability" specifically includes: assuming the probability of a voxel of the voxel model occupied in the bounding box as 1 and the probability of a free voxel as 0, and obtaining spatial distribution of each frame of voxel model in the minimum common bounding box.

Preferably, the "reducing the dimensions of the sample space" specifically includes reducing the dimensions of the sample space through an LLE dimensionality reduction algorithm.

Preferably, the "obtaining a characteristic variable capable of characterizing the voxel model according to the intrinsic parameters, the volumetric characteristic, and the areal characteristic" specifically includes: merging the intrinsic parameters $\psi=[\psi_1, \psi_2, \ldots, \psi_m]$, the volumetric characteristic V and the areal characteristic S, and obtaining characteristic variables $\Gamma$ capable of characterizing different states of the voxel model, where $\Gamma=[VS \ldots \psi_1, \psi_2, \ldots, \psi_m]^T$.

As compared with the prior art, the present invention has the following advantages:

In the present invention, valid volumetric and areal physical variables are extracted from the voxel model of the thoracoabdominal surface and data structure analysis is performed to extract the intrinsic parameters after dimensionality reduction, so as to obtain characteristic variables characterizing different states of the voxel model. By extending the method for characterization of limited body-surface marking points into a method for characterization of the curved surface model of the whole body surface, the body-surface respiratory motion information that is characterized becomes more comprehensive. This method can address the problem of existing methods that the respiratory motion phenomenon is described insufficiently due to use of sparse perception data.

BRIEF DESCRIPTION OF THE DRAWINGS

FIG. 7 shows a respiratory characteristic curve reduced to 6 dimensions through an LLE dimensionality reduction algorithm, in which FIGS. 7(a), 7(b), 7(c), 7(d), 7(e), and 7(f) represent characteristic variation over time in each dimension after dimensionality reduction.

DETAILED DESCRIPTION OF THE PREFERRED EMBODIMENTS

The present invention is to be further explained in the following with reference to the drawings and specific embodiments, so that those skilled in the art can better understand the present invention and implement it, but the embodiments listed are not to be intended as limitations of the present invention.

Referring to FIGS. 1 to 7, a method for characterization of respiratory characteristics based on a voxel model disclosed in the present invention includes the following steps.

Figure 1:
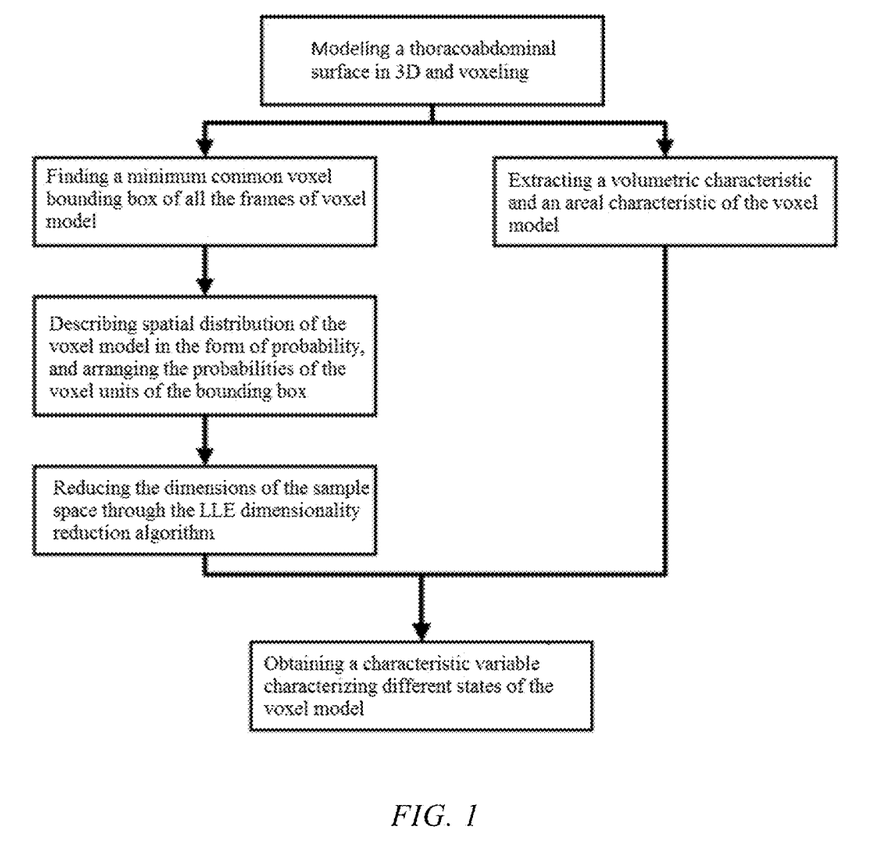
FIG. 1 is a flow diagram of a method according to the present invention.

Step 1: successively capturing, by a camera, multiple frames of depth image of a thoracoabdominal surface of human body and modelling the multiple frames of depth image in 3D to obtain multiple frames of voxel model in time series, which specifically includes the following steps.

S11 successively capturing, by two stationary RGB-D cameras, multiple frames of depth image of thoracoabdominal surface of human body in motion.

S12 denoising point cloud data in the depth image through a filter algorithm, smoothening the point cloud through a moving least square method, and merging the point cloud data through an ICP algorithm.

S13 splitting human body data from medical platform background data in the depth image through threshold filtering.

S14 constructing a surface model into a closed model through border interpolation.

S15 quick fitting the three-dimensional curved surface of the human body surface through Poisson's reconstruction.

S16 building a three-dimensional voxel model of thoracoabdominal part of human body through an Octomap to obtain multiple frames of voxel model in time series.

Figure 2:
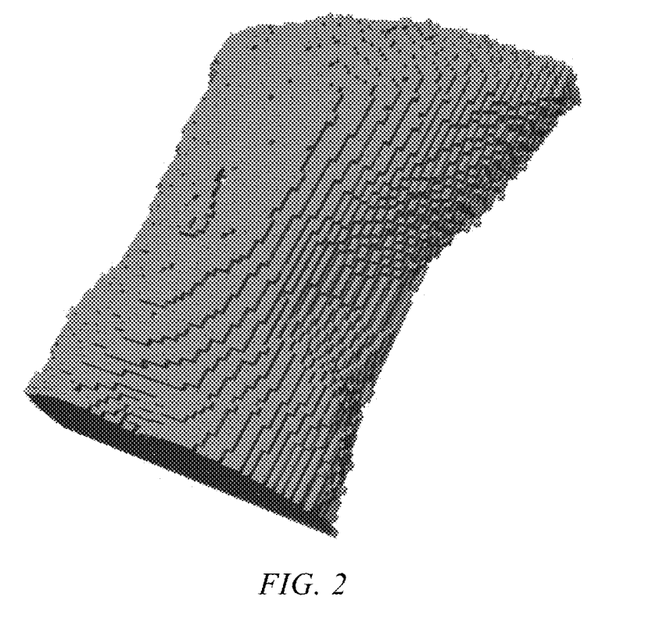
FIG. 2 shows a voxel model of the thoracoabdominal surface.

As shown in FIG. 2, the thoracoabdominal surface of human body captured during respiration by two depth cameras is modelled in 3D through a reconstruction algorithm and the 3D model is voxelated through an Octomap.

Step 2: traversing a voxel unit of the multiple frames of voxel model and extracting a volumetric characteristic V and an areal characteristic S of the multiple frames of voxel model. The "volumetric characteristic" is the overall volumetric variation state characteristic of the multiple frames of voxel model, and the "areal characteristic" is the overall outer-layer surface area variation state characteristic of the multiple frames of voxel model.

Figure 3:
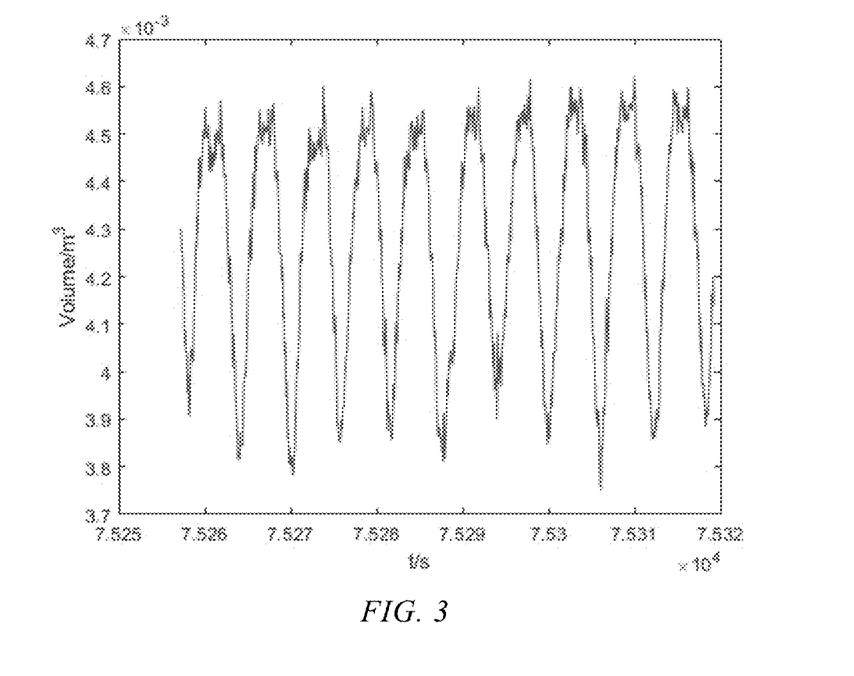
FIG. 3 shows a volumetric characteristic curve of a voxel model.

FIG. 3 shows a volumetric variation curve of a voxel model in time series. The voxel units of each frame of voxel model are traversed and volumes of the voxel units are accumulated to reflect volumetric variation in time series.

Figure 4:
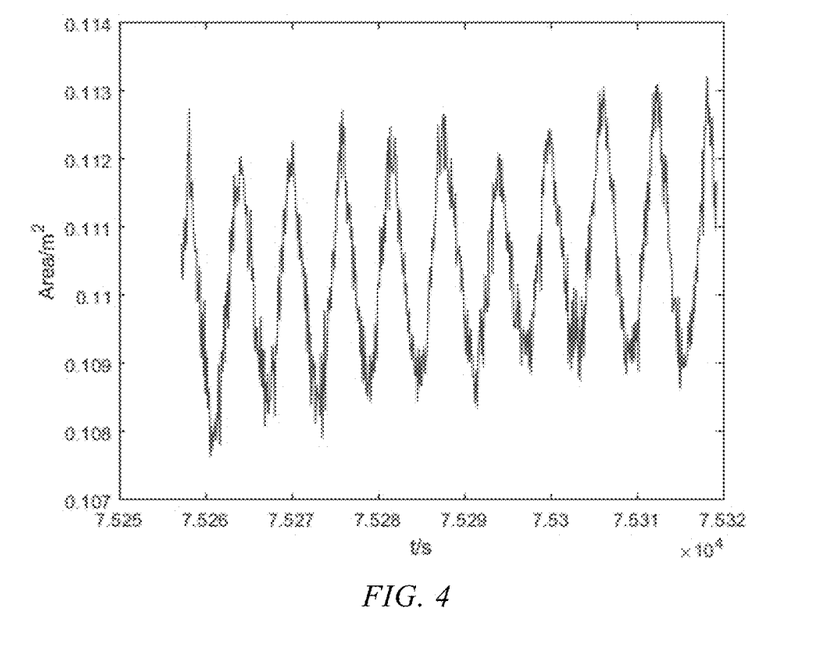
FIG. 4 shows an areal characteristic curve of a voxel model.

FIG. 4 shows an areal variation curve of a voxel model in time series. The voxel units of each frame of voxel model are traversed and areas of the outer-layer voxel units are accumulated to reflect areal variation in time series.

Step 3: acquiring a minimum common voxel bounding box of the multiple frames of voxel model.

Figure 5:
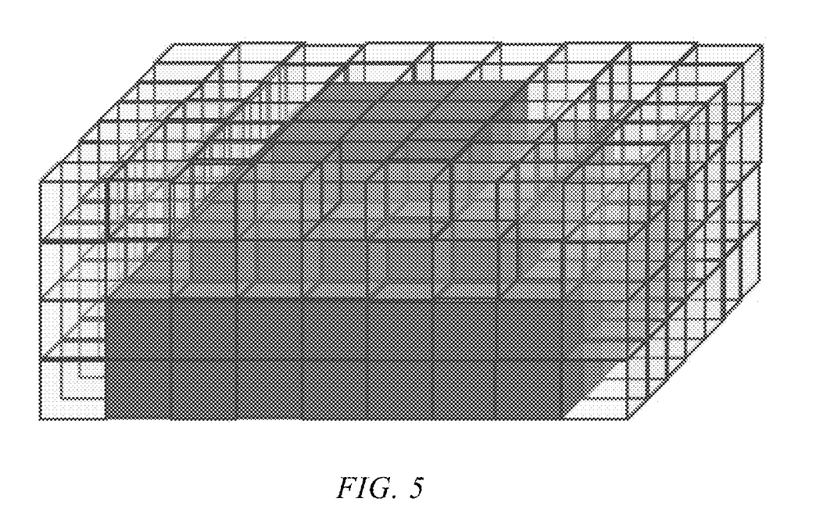
FIG. 5 shows a minimum common bounding box containing a voxel model.

FIG. 5 shows a schematic structural view of acquired minimum common bounding boxes of all the frames of voxel model. Each of the frames of voxel model has its own bounding box and these bounding boxes are of different sizes. For unified analysis, it is necessary to find a common minimum bounding box. This bounding box needs to satisfy two conditions: first, it is applicable to each frame of voxel model (capable of enclosing the voxel model); and secondly, the bounding box has the minimum size (with reduced amount of computation).

First, each frame of voxel model is represented as $M_i \in M$ and M is traversed.

Then the minimum bounding box of $M_i$ is calculated, and the length, width and height of the bounding box are recorded as $L_{Mi} \in L$, $W_{Mi} \in W$, $H_{Mi} \in H$.

Finally, $L_{max}$, $L_{min}$, $W_{max}$, $W_{min}$, $H_{max}$, $H_{min}$ are found in L, W, H to construct a minimum common voxel bounding box B that partitions the space according to the voxel resolution of M.

Step 4: describing spatial distribution of the multiple frames of voxel model in the form of probability and arranging the probabilities of the minimum voxel bounding boxes of individual frames of voxel model to construct a sample space of superhigh-dimensional vectors.

Figure 6:
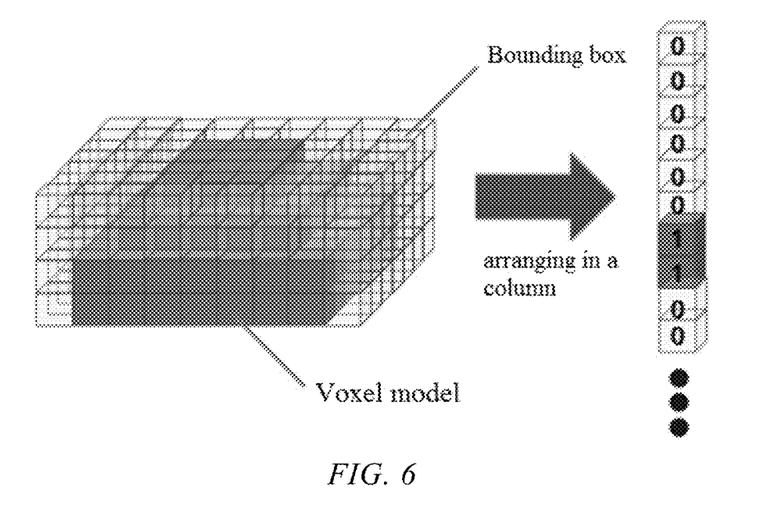
FIG. 6 is a schematic view of probabilities of voxel units arranged in a column.

FIG. 6 shows a superhigh-dimensional sample constructed from a single voxel model. The probability of the voxel of the voxel model occupied in the bounding box is assumed as 1 and the probability of the free voxel is assumed as 0. The probabilities of all the voxel units in the bounding box are arranged in a column to construct a superhigh-dimensional column vector. The operations described above are performed on all the frames of voxel model to construct a sample space.

Step 5: reducing the dimensions of the sample space to obtain intrinsic parameters after dimensionality reduction.

Figure 7:
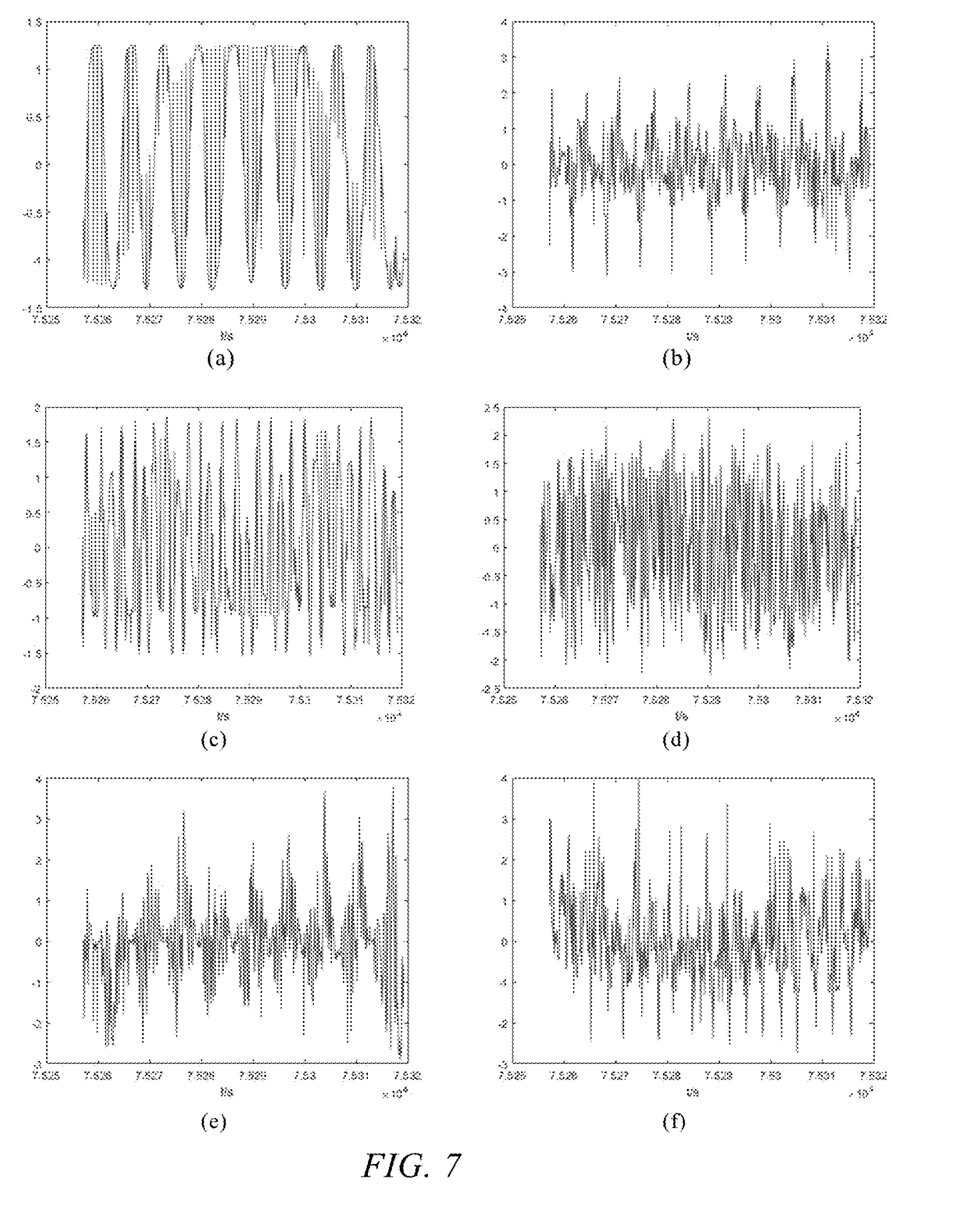

For example, the dimensions are reduced to 6 dimensions, and FIG. 7 shows a respiratory characteristic curve of a voxel model extracted to 6 dimensions through an LLE dimensionality reduction algorithm, collectively characterizing the feature of variation of the respiratory motion of the whole thoracoabdominal cavity voxel model over time.

Step 6: obtaining a characteristic variable capable of characterizing the voxel model according to the intrinsic parameters, the volumetric characteristic, and the areal characteristic.

The intrinsic parameters $\psi=[\psi_1, \psi_2 \ldots, \psi_m]$, the volumetric characteristic V and the areal characteristic S are merged to obtain a characteristic variable $\Gamma$ capable of characterizing different states of the voxel model, where $\Gamma = [VS \ldots \psi_1, \psi_2, \ldots, \psi_m]^T$.

As shown in FIGS. 3, 4 and 7, it can be seen from the results of characterization of respiratory motion based on the voxel model obtained using the method provided by the present invention that, all the characteristics reflect respiratory characteristic variation and each of them reflects a different respiratory characteristic, showing the diversity of thoracoabdominal surface respiratory characteristics. In contrast to conventional methods for characterization of limited body-surface marking points, combined characteristic variables of multiple characteristics can characterize body-surface motion information more comprehensively. The method of the present invention can provide characterization of the whole thoracoabdominal surface respiratory motion.

In conventional methods for characterization of body-surface marking points, the body-surface motion is characterized by way of x, y and z motions of limited number of body-surface marking points, which has the drawback of incomprehensive characterized information. According to the present invention, respiration characterization is based on a voxel model, whereby respiratory characteristics are extracted from the whole body surface model and volume, area, and dimensionality reduction results all reflect the characteristic information of the whole model, which features more comprehensive characterization. Also, the characteristic described above are combined into one characteristic vector as the characterization vector that is finally obtained by this method, which facilitates subsequent construction of a model of association with the internal tumor motion. Therefore, the present invention has promising application prospects.

The embodiments described above are only preferred embodiments intended for full explanation of the present invention, and the scope of protection of the present invention is not limited thereto. Equivalent substitutions or variants made by those skilled in the art on the basis of the present invention shall fall within the scope of protection of the present invention. The scope of protection of the present invention shall be defined by the claims.

What is claimed is:

1. A method for characterization of respiratory characteristics based on a voxel model, comprising steps of:
successively capturing, by a camera, multiple frames of depth image of a thoracoabdominal surface of a human body and performing modelling the multiple frames of depth image in 3D to obtain multiple frames of voxel model in time series;
traversing voxel units of the multiple frames of voxel model and extracting a volumetric characteristic and an areal characteristic of the multiple frames of voxel model;
acquiring a minimum common voxel bounding box of the multiple frames of voxel model;
describing spatial distribution of the multiple frames of voxel model in the form of probability and arranging the probabilities of the minimum voxel bounding boxes of individual frames of voxel model to construct a sample space of super-high dimensional vectors;
reducing the dimensions of the sample space to obtain intrinsic parameters after dimensionality reduction; and
obtaining a characteristic variable capable of characterizing the voxel model according to the intrinsic parameters, the volumetric characteristic, and the areal characteristic,
wherein the acquiring a minimum common voxel bounding box of the multiple frames of voxel model" comprises:
representing each frame of the voxel model by $M_i$ and letting $M_i \in M$, M being all the frames of voxel model;
traversing M, calculating the minimum bounding box of $M_i$, recording the length $L_{M_i}$, width $W_{M_i}$, and height $H_{M_i}$ of the minimum bounding box, letting $L_{M_i} \in L$, $W_{M_i} \in W$, $H_{M_i} \in H$, where L is the set of the lengths of the minimum bounding boxes of all the frames of voxel model, W is the set of the widths of the minimum bounding boxes of all the frames of voxel model, and H is the set of the heights of the minimum bounding boxes of all the frames of voxel model; and
finding $L_{max}$, $L_{min}$, $W_{max}$, $W_{min}$, $H_{max}$, $H_{min}$ in L, W, H to construct a minimum common voxel bounding box H that partitions the space according to the voxel resolution of M.

2. The method for characterization of respiratory characteristics based on a voxel model of claim 1, wherein the "volumetric characteristic" is the overall volumetric variation state characteristic of the multiple frames of voxel model.

3. The method for characterization of respiratory characteristics based on a voxel model of claim 1, wherein the "areal characteristic" is the overall outer-layer surface area variation state characteristic of the multiple frames of voxel model.

4. The method for characterization of respiratory characteristics based on a voxel model of claim 1, wherein the "successively capturing, by a camera, multiple frames of depth image of a thoracoabdominal surface of a human body and modelling the multiple frames of depth image in 3D to obtain multiple frames of voxel model in time series" comprises the following steps:

S11 successively capturing, by two stationary RGB-D cameras, multiple frames of depth image of thoracoabdominal surface of human body in motion;

S12 denoising point cloud data in the depth image through a filter algorithm, smoothening the point cloud through a moving least square method, and merging the point cloud data through an ICP algorithm;

S13 splitting human body data from medical platform background data in the depth image through threshold filtering;

S14 constructing a surface model into a closed model through border interpolation;

S15 quick fitting the three-dimensional curved surface of human body surface through Poisson's reconstruction; and S16 building a three-dimensional voxel model of thoracoabdominal part of human body through an Octomap to obtain multiple frames of voxel model in time series.

5. The method for characterization of respiratory characteristics based on a voxel model of claim 1, wherein the "describing spatial distribution of the multiple frames of voxel model in the form of probability" comprises:

assuming the probability of the voxel of the voxel model occupied in the bounding box as 1 and the probability of the free voxel as 0, and obtaining spatial distribution of each frame of voxel model in the minimum common bounding box.

6. The method for characterization of respiratory characteristics based on a voxel model of claim 1, wherein the "reducing the dimensions of the sample space" comprises reducing the dimensions of the sample space through the LLE dimensionality reduction algorithm.

7. The method for characterization of respiratory characteristics based on a voxel model of claim 1, wherein the "obtaining a characteristic variable capable of characterizing the voxel model according to the intrinsic parameters, the volumetric characteristic, and the areal characteristic" comprises:

merging the intrinsic parameters $\psi=[\psi_1, \psi_2, \ldots, \psi_m]$, the volumetric characteristic V and the areal characteristic S, and obtaining a characteristic variable $\Gamma$ capable of characterizing different states of the voxel model, where $\Gamma=[VS \ldots \psi_1, \psi_2, \ldots, \psi_m]^T$.

* * * * *